(12) United States Patent
Boudreaux et al.

(10) Patent No.: US 9,999,408 B2
(45) Date of Patent: Jun. 19, 2018

(54) SURGICAL INSTRUMENT WITH FLUID FILLABLE BUTTRESS

(75) Inventors: Chad P. Boudreaux, Cincinnati, OH (US); Stephen J. Balek, Springboro, OH (US); Matthew D. Holcomb, Lebanon, OH (US); Edward A. Rhad, Fairfield, OH (US); Donald F. Wilson, Jr., Raleigh, NC (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1793 days.

(21) Appl. No.: 13/232,401

(22) Filed: Sep. 14, 2011

(65) Prior Publication Data

US 2013/0062391 A1   Mar. 14, 2013

(51) Int. Cl.
| | | |
|---|---|---|
| A61B 17/04 | (2006.01) | |
| A61B 17/10 | (2006.01) | |
| A61B 17/072 | (2006.01) | |
| A61B 17/00 | (2006.01) | |

(52) U.S. Cl.
CPC .. *A61B 17/00491* (2013.01); *A61B 17/07207* (2013.01); *A61B 17/07292* (2013.01); *A61B 2017/00495* (2013.01)

(58) Field of Classification Search
CPC  A61K 33/00; A61K 38/4833; A61B 17/0401; A61B 17/068; A61B 17/0469; A61B 17/3468; A61B 17/00234; A61B 17/0643; A61B 17/08; A61B 17/1764; A61B 17/0644; A61B 17/10; A61B 17/11; A61B 17/320016

USPC .......................................... 227/175.1–182.1
See application file for complete search history.

(56) References Cited

U.S. PATENT DOCUMENTS

| | | |
|---|---|---|
| 2,303,131 A | 11/1942 | Morgan |
| 3,364,200 A | 1/1968 | Ashton et al. |
| 3,496,940 A | 2/1970 | Steinman |
| 3,526,228 A | 9/1970 | Lyng |
| 4,222,383 A | 9/1980 | Schossow |
| 4,513,746 A | 4/1985 | Aranyi |
| 4,549,545 A | 10/1985 | Levy |
| 4,610,250 A | 9/1986 | Green |

(Continued)

FOREIGN PATENT DOCUMENTS

| | | |
|---|---|---|
| CA | 481943 | 2/1947 |
| CN | 1221443 A | 6/1999 |

(Continued)

OTHER PUBLICATIONS

International Search Report dated Dec. 7, 2012 for Application No. PCT/US2012/054401.

(Continued)

*Primary Examiner* — Robert Long
(74) *Attorney, Agent, or Firm* — Frost Brown Todd LLC

(57) ABSTRACT

An apparatus comprises a surgical instrument and a buttress configured to hold a fluid adhesive. In some versions, the buttress contains a two-part fluid adhesive where two fluid materials form a fluid adhesive when combined. In some versions, the buttress is configured to be compressed by the surgical instrument thereby pressurizing a portion of the buttress. Thereafter, the buttress may be severed and the pressurized region may be operable to urge the fluid adhesive to a tissue site.

20 Claims, 16 Drawing Sheets

(56) References Cited

U.S. PATENT DOCUMENTS

| | | |
|---|---|---|
| 4,693,720 A | 9/1987 | Scharnberg et al. |
| 4,805,823 A | 2/1989 | Rothfuss |
| 5,011,493 A | 4/1991 | Belykh et al. |
| 5,064,057 A | 11/1991 | Iwatsuki et al. |
| 5,263,629 A | 11/1993 | Trumbull et al. |
| 5,282,829 A | 2/1994 | Hermes |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfinan et al. |
| 5,411,193 A | 5/1995 | Culp |
| 5,415,334 A | 5/1995 | Williamson, IV et al. |
| 5,465,895 A | 11/1995 | Knodel et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | Mckean et al. |
| 5,565,210 A | 10/1996 | Rosenthal et al. |
| 5,597,107 A | 1/1997 | Knodel et al. |
| 5,607,590 A | 3/1997 | Simizu |
| 5,607,686 A | 3/1997 | Totakura et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,810,855 A | 9/1998 | Rayburn et al. |
| 5,814,055 A | 9/1998 | Knodel et al. |
| 5,814,057 A | 9/1998 | Oi et al. |
| 5,843,096 A | 12/1998 | Igaki et al. |
| 5,902,312 A | 5/1999 | Frater et al. |
| 5,997,895 A | 12/1999 | Narotam et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,814,741 B2 | 11/2004 | Bowman et al. |
| 6,835,336 B2 | 12/2004 | Watt |
| 6,921,412 B1 | 7/2005 | Black et al. |
| 6,962,594 B1 | 11/2005 | Thevenet |
| 6,978,921 B2 | 12/2005 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,143,923 B2 | 12/2006 | Shelton, IV et al. |
| 7,147,138 B2 | 12/2006 | Shelton, IV |
| 7,207,471 B2 | 4/2007 | Heinrich et al. |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,517,356 B2 | 4/2009 | Heinrich |
| 7,607,557 B2 | 10/2009 | Shelton, IV et al. |
| 7,673,783 B2 * | 3/2010 | Morgan et al. ............ 227/180.1 |
| 7,708,180 B2 | 5/2010 | Murray et al. |
| 7,721,930 B2 | 5/2010 | McKenna et al. |
| 7,738,971 B2 | 6/2010 | Swayze et al. |
| 7,845,533 B2 | 12/2010 | Marczyk et al. |
| 7,845,536 B2 * | 12/2010 | Viola et al. ............... 227/179.1 |
| 7,922,743 B2 | 4/2011 | Heinrich et al. |
| 8,066,732 B2 * | 11/2011 | Paul et al. .................... 606/195 |
| 8,066,733 B2 * | 11/2011 | Paul et al. .................... 606/195 |
| 8,333,786 B2 * | 12/2012 | Mirizzi et al. ............... 606/200 |
| 8,464,925 B2 * | 6/2013 | Hull et al. ................. 227/179.1 |
| 8,486,155 B2 * | 7/2013 | McAlister et al. ......... 623/23.72 |
| 8,491,526 B2 * | 7/2013 | Cronin et al. .................. 604/82 |
| 8,511,533 B2 | 8/2013 | Viola et al. |
| 8,568,446 B2 * | 10/2013 | Kurokawa et al. ............ 606/213 |
| 8,684,250 B2 * | 4/2014 | Bettuchi et al. ............ 227/179.1 |
| 2002/0165559 A1 | 11/2002 | Grant et al. |
| 2003/0120284 A1 | 6/2003 | Palacios et al. |
| 2003/0183671 A1 | 10/2003 | Moofadian et al. |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0101834 A1 | 5/2005 | Merade |
| 2005/0107810 A1 | 5/2005 | Morales et al. |
| 2005/0145671 A1 | 7/2005 | Viola |
| 2005/0154403 A1 | 7/2005 | Sauer et al. |
| 2005/0245965 A1 | 11/2005 | Orban, III et al. |
| 2005/0249772 A1 | 11/2005 | Maliviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0004407 A1 | 1/2006 | Hiles et al. |
| 2006/0047312 A1 | 3/2006 | Olmo et al. |
| 2006/0093655 A1 | 5/2006 | Bar et al. |
| 2006/0094318 A1 | 5/2006 | Matsuda et al. |
| 2006/0108393 A1 * | 5/2006 | Heinrich et al. ............ 227/179.1 |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034668 A1 * | 2/2007 | Holsten et al. ............ 227/179.1 |
| 2007/0034669 A1 | 2/2007 | de la Tare et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0102473 A1 * | 5/2007 | Shelton et al. ............ 227/175.1 |
| 2007/0106317 A1 * | 5/2007 | Shelton et al. ................ 606/170 |
| 2007/0112360 A1 | 5/2007 | De Deyne et al. |
| 2007/0128243 A1 | 6/2007 | Serafica et al. |
| 2007/0131732 A1 | 6/2007 | Holsten et al. |
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0039871 A1 | 2/2008 | Wallace et al. |
| 2008/0077131 A1 | 3/2008 | Yates |
| 2008/0078800 A1 | 4/2008 | Hess et al. |

(56) References Cited

U.S. PATENT DOCUMENTS

| | | |
|---|---|---|
| 2008/0078801 A1 | 4/2008 | Shelton, IV et al. |
| 2008/0078802 A1 | 4/2008 | Hess et al. |
| 2008/0078803 A1 | 4/2008 | Shelton, IV et al. |
| 2008/0078804 A1 | 4/2008 | Shelton, IV et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |
| 2008/0110959 A1 | 5/2008 | Orban, III et al. |
| 2008/0114381 A1 | 5/2008 | Voegle et al. |
| 2008/0114385 A1 | 5/2008 | Byrum et al. |
| 2008/0114399 A1 | 5/2008 | Bonutti |
| 2008/0125812 A1 | 5/2008 | Zubik et al. |
| 2008/0128469 A1 | 6/2008 | Dalessandro et al. |
| 2008/0140115 A1 | 6/2008 | Stopek |
| 2008/0200949 A1 | 8/2008 | Hiles et al. |
| 2008/0314960 A1 | 12/2008 | Marczyk et al. |
| 2009/0001122 A1 | 1/2009 | Prommersberger et al. |
| 2009/0076510 A1 | 3/2009 | Bell et al. |
| 2009/0092651 A1* | 4/2009 | Shah et al. .................. 424/422 |
| 2009/0118747 A1 | 5/2009 | Bettuchi et al. |
| 2009/0120994 A1* | 5/2009 | Murray et al. ............. 227/180.1 |
| 2011/0282446 A1* | 11/2011 | Schulte et al. ............. 623/11.11 |
| 2012/0080344 A1 | 4/2012 | Shelton |
| 2013/0062393 A1* | 3/2013 | Bruewer et al. ........... 227/176.1 |
| 2013/0087599 A1* | 4/2013 | Krumanaker et al. ..... 227/176.1 |

FOREIGN PATENT DOCUMENTS

| | | |
|---|---|---|
| EP | 328 401 | 8/1989 |
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | H06-327684 A | 11/1994 |
| JP | 11309151 | 11/1999 |
| WO | WO 1993/010731 | 6/1993 |
| WO | WO 1998/038923 | 9/1998 |
| WO | WO 2001/017446 | 3/2001 |
| WO | WO 2002/009593 | 2/2002 |
| WO | WO 2002/022184 | 3/2002 |
| WO | WO 2003/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |
| WO | WO 2011/143184 | 11/2011 |

OTHER PUBLICATIONS

Abstract for FR2789885.
Abstract for FR2850281.
Abstract for JP1072740
Abstract for JP11309151.
Abstract for JP3146773.
Abstract for JP5076586.
International Preliminary Report on Patentability dated Mar. 18, 2014 for Application No. PCT/US2012/054401.
Chinese Office Action, Notification of First Office Action, and Search Report dated Nov. 2, 2015 for Application No. CN 201280054928.7, 11 pgs.
Japanese Office Action, Notification of Reason for Refusal, dated Jul. 26, 2016 for Application No. JP 2014-530717, 6 pgs.
Mexican Exam Report dated Apr. 27, 2017 for Application No. MX/a/2014/002976, 3 pgs.

* cited by examiner

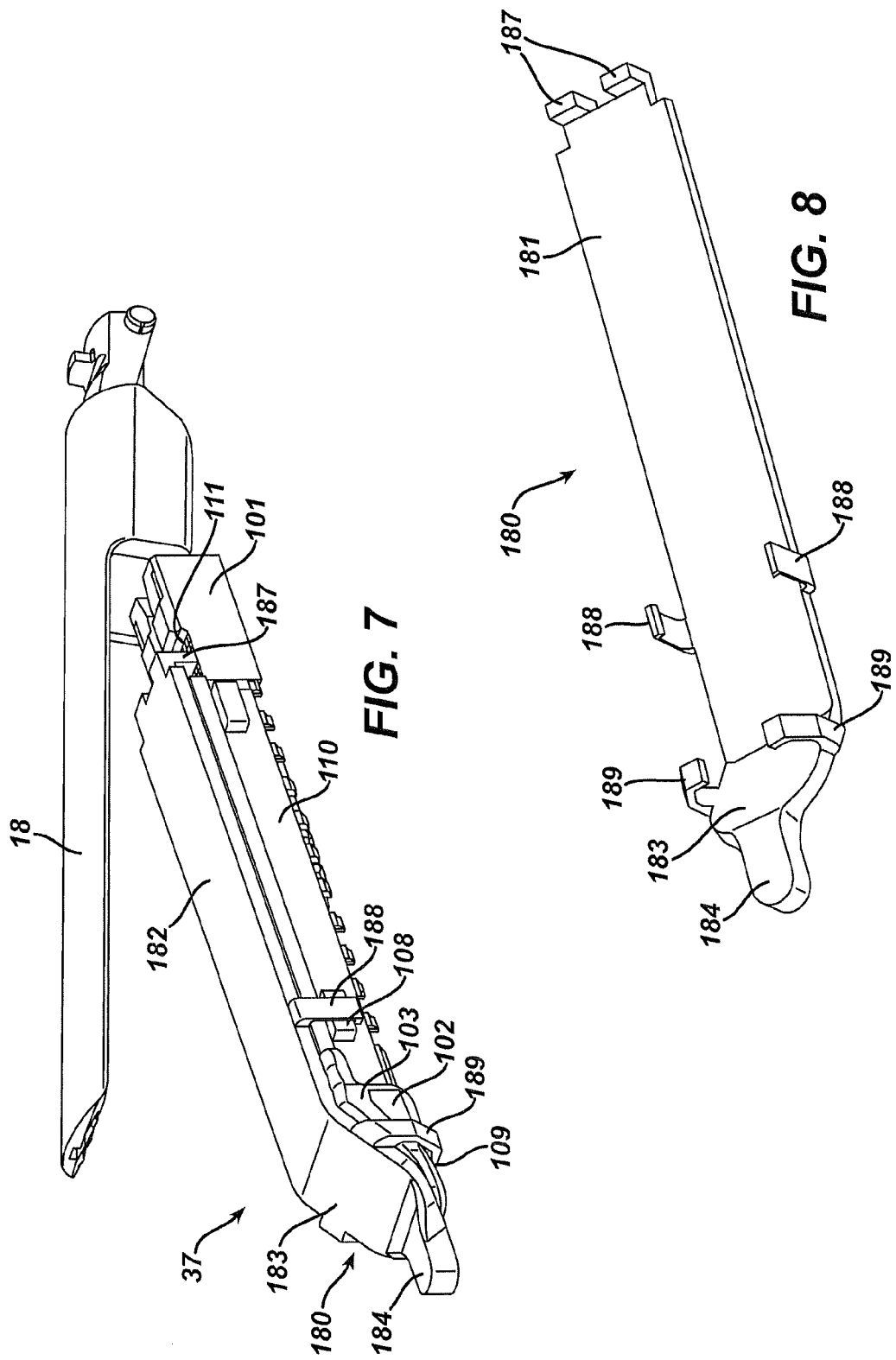

SURGICAL INSTRUMENT WITH FLUID FILLABLE BUTTRESS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7 depicts a perspective view of a retainer cap with the end effector of FIG. 2;

FIG. 8 depicts a perspective underside view of the retainer cap of FIG. 7;

Figure 1A:
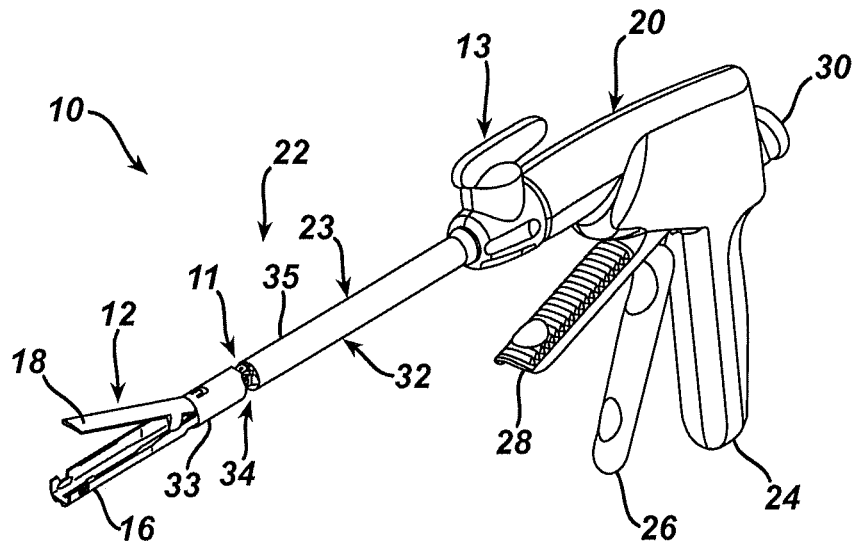
FIG. 1A depicts a perspective view of an articulating surgical instrument with an end effector in a nonarticulated position.
Figure 1B:
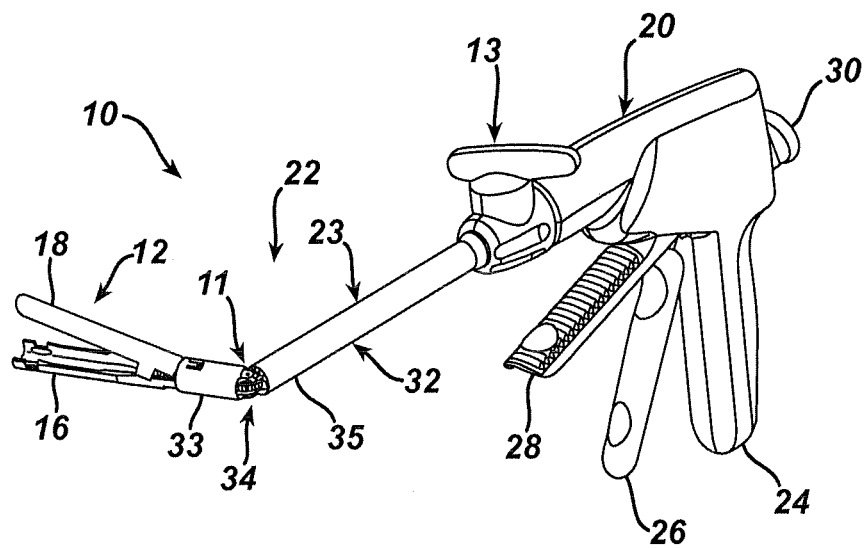
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
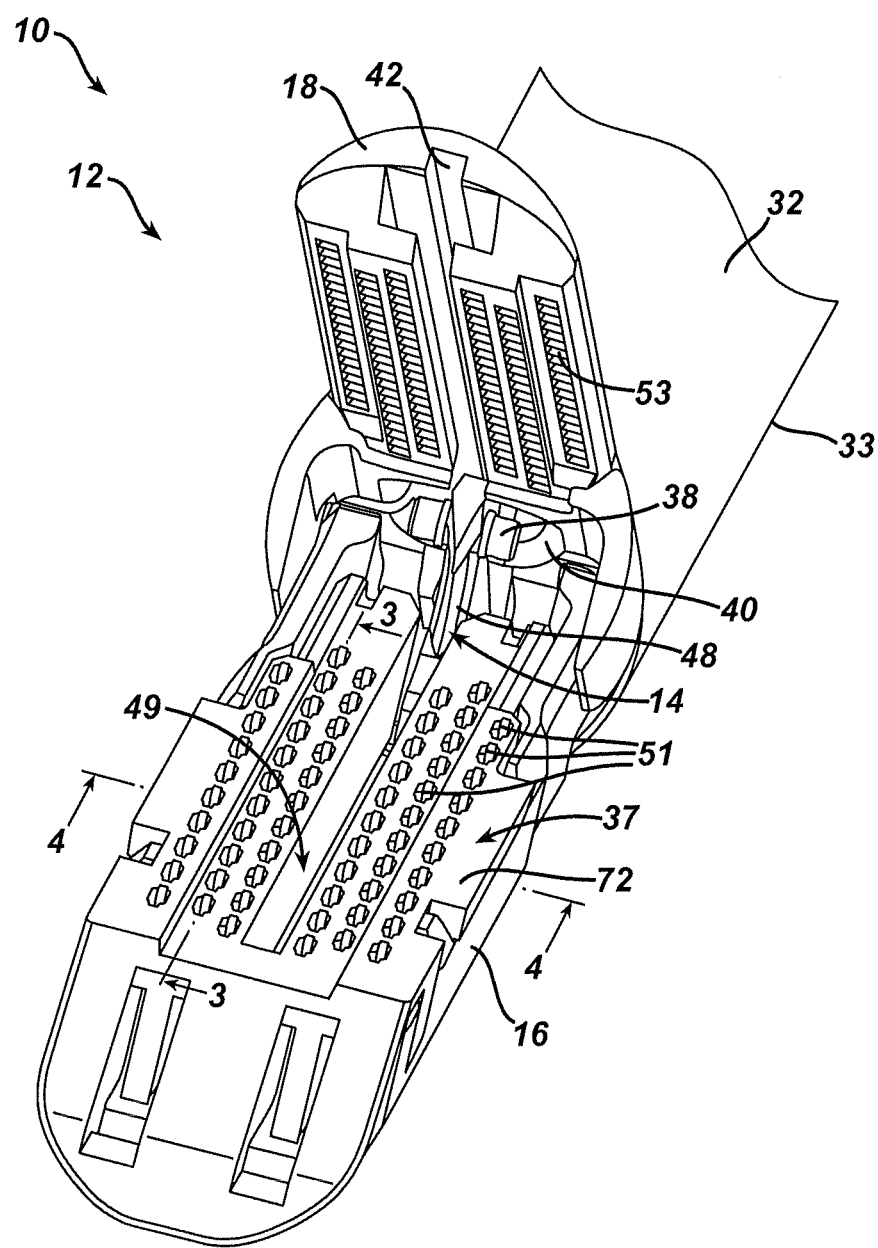
FIG. 2 depicts a perspective view of an opened end effector of the surgical instrument of FIGS. 1A-1B.
Figure 3A:
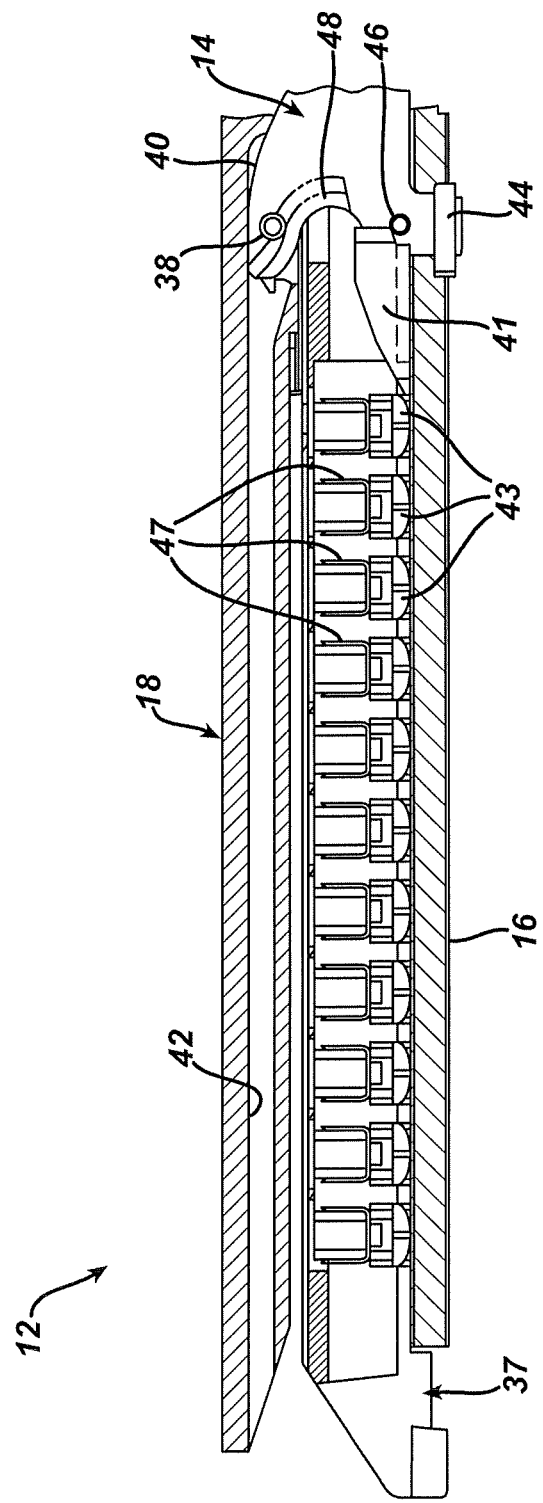
FIG. 3A depicts a side cross-sectional view of the end effector of FIG. 2, taken along line 3-3 of FIG. 2, with the firing bar in a proximal position.
Figure 3B:
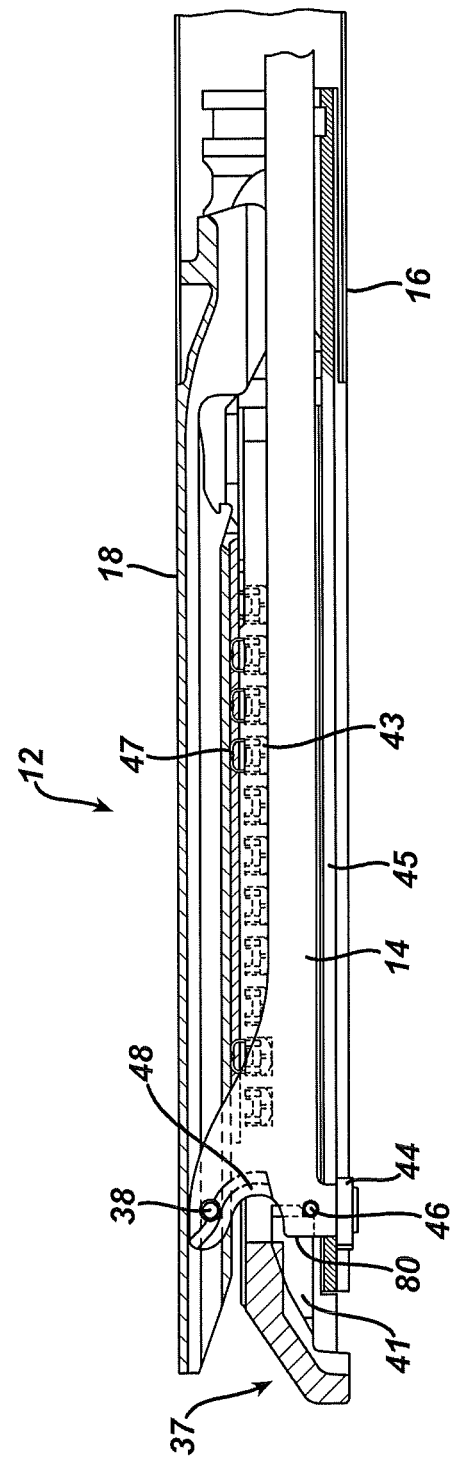
FIG. 3B depicts a side cross-sectional view of the end effector of FIG. 2, taken along line 3-3 of FIG. 2, but showing the firing bar in a distal position.
Figure 4:
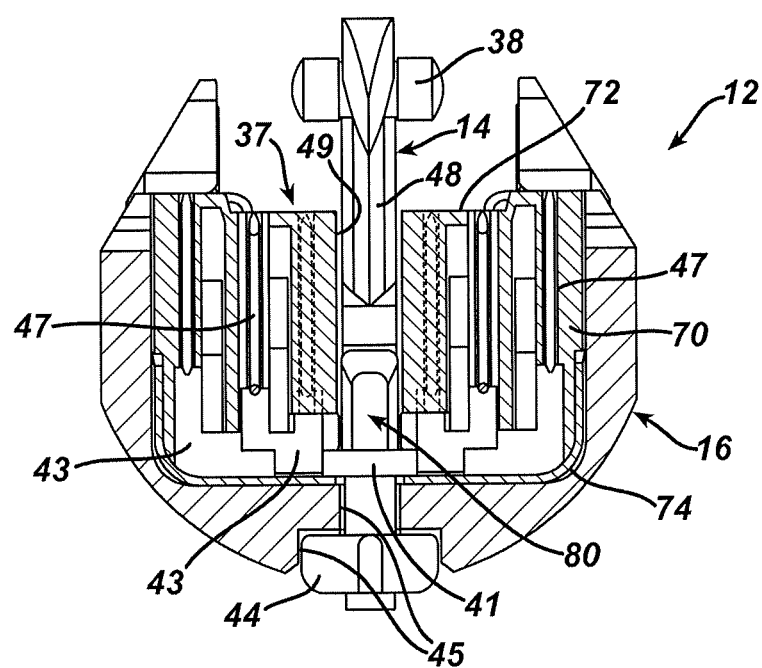
FIG. 4 depicts an end cross-sectional view of the end effector of FIG. 2, taken along line 4-4 of FIG. 2.
Figure 5:
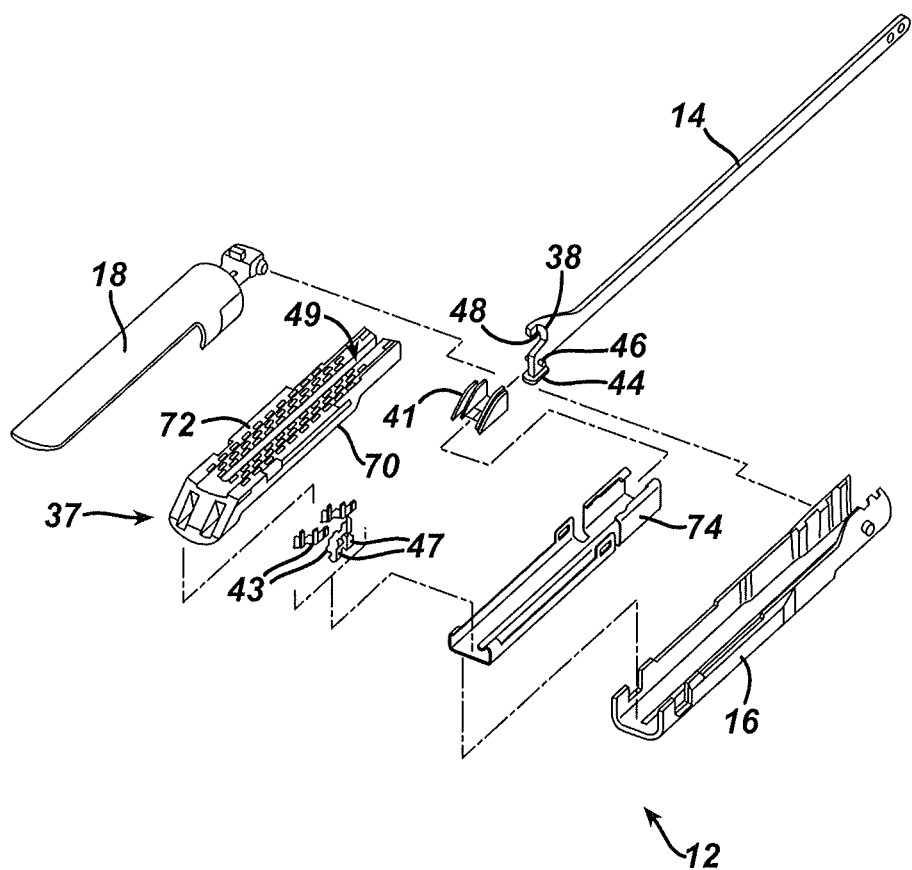
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (70) on one side of vertical slot (49), with another set of three rows of staple apertures (51) being formed through upper deck (70) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
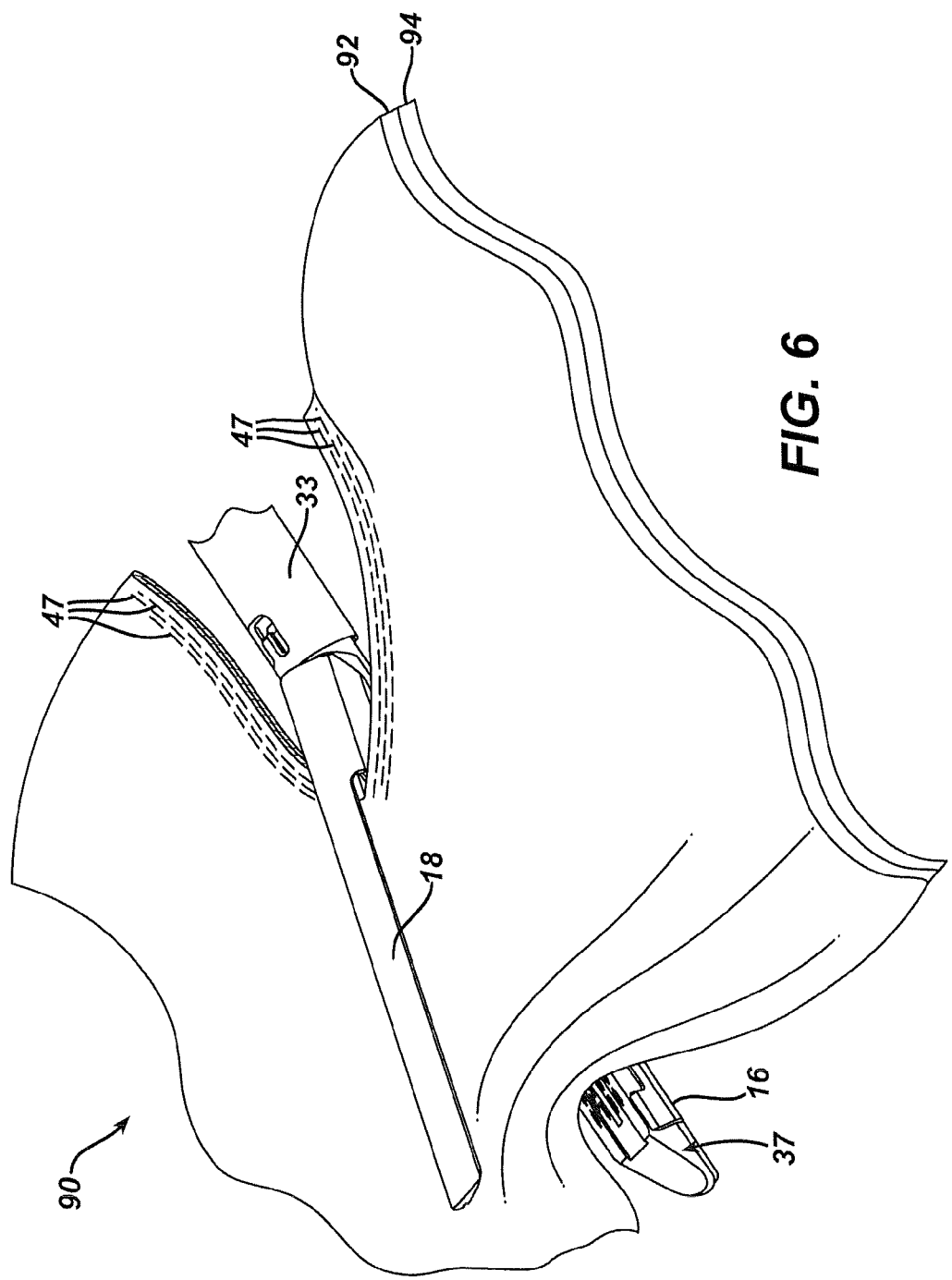
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Cover

Figure 9:
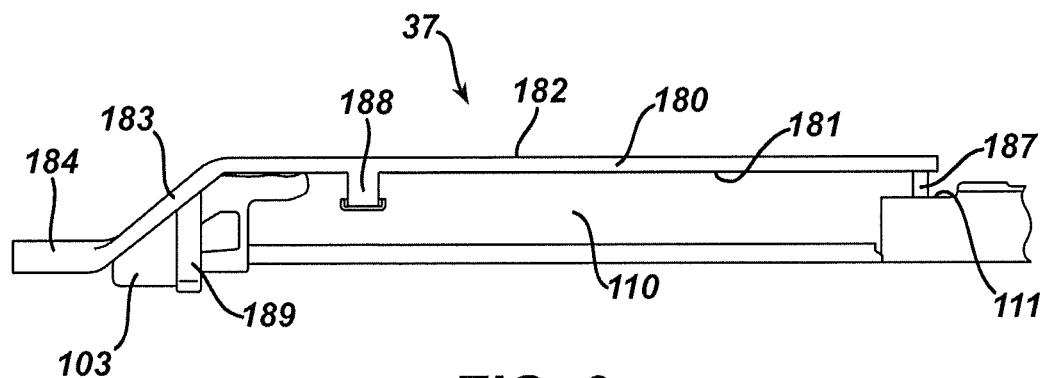
FIG. 9 depicts a side view of the retainer cap with the end effector of FIG. 7.

FIGS. 7-9 show an exemplary staple cartridge (37) retainer cap (180), which may be attached to staple cartridge (37). It should be understood that retainer cap (180) may be configured and operable in accordance with any of the teachings of U.S. Pub. No. 2012/0080344, published Apr. 5, 2012, entitled "Implantable Fastener Cartridge Comprising a Support Retainer", now abandoned, the entire disclosure of which is incorporated by reference herein. Retainer cap (180) is operable to prevent, or at least inhibit, a clinician's thumb, for example, from contacting the tips of staples (47) positioned within staple cartridge (37) when staple cartridge (37) is inserted into lower jaw (16) of end effector (12). In addition or in the alternative, it may prevent staples (47) from inadvertently falling out of the cartridge. Referring now to FIGS. 7 and 8, retainer cap (180) of the present example includes bottom surface (181) and top surface (182), which can provide a pushing surface for the clinician to apply a downward force thereto, for example. In one merely exemplary use, the clinician may grab handle portion (184) of retainer cap (180), align support portion (110) of staple cartridge (37) with lower jaw (16) of end effector (12), and at least partially insert staple cartridge (37) within lower jaw (16) of end effector (12). Thereafter, the clinician can completely seat staple cartridge (37) in lower jaw (16) of end effector (12) by applying the downward force to top surface (182) of retainer cap (180) which can transmit the downward force directly to support portion (110). In the present example, retainer cap (180) comprises proximal supports (187) which extend downwardly and contact deck surface (111) of the support portion. Retainer cap (180) further comprises distal support portion (183), which abuts nose (103). When a downward force is applied to retainer cap (180), the downward force can be transmitted through proximal supports (187) and/or distal support portion (183). In some exemplary versions, at least some of the supports may not be in contact with the top of support portion (110) before the downward force is applied to retainer cap (180); however, in some versions, retainer cap (180) can be operable to flex, or move, downwardly until retainer cap (180) touches the top of support portion (110). At such point, the downward flexure, or movement, of retainer cap (180) can be impeded, or at least substantially impeded, from flexing further.

As described above, retainer cap (180) can be attached to staple cartridge (37) and can be used to manipulate the position of staple cartridge (37). In some versions, retainer cap (180) can comprise any suitable number of gripping members which can be operable to releasably hold retainer cap (180) to support portion (110) of staple cartridge (37), for example. For instance, in the present example, retainer cap (180) comprises latch arms (188, 189). Latch arms (189) extend around the sides of nose (103) and engage bottom surface (109) (FIG. 7) of nose (103). Similarly, latch arms (188) extend around the sides of lock projections (108) extending from support portion (110) and engage the bottom surfaces of lock projections (108). These latch arms (188) are operable to position retainer cap (180) over the zone or region in which the staples (47) are stored within support portion (110). In any event, once staple cartridge (37) has been suitably positioned, retainer cap (180) can be detached from staple cartridge (37). Of course, any other suitable components or features may be used to provide releasable coupling of retainer cap (180) to staple cartridge (37). In some versions, the clinician may apply an upward lifting force to handle (184) in order to detach the distal end of retainer cap (180) from distal end (102) of staple cartridge (37). In at least one such embodiment, latch arms (188, 189) may flex outwardly as handle (184) is lifted upwardly such that latch arms (188, 189) may flex around lock projections (108) and nose (103), respectively. Thereafter, the proximal end of retainer cap (180) may be lifted away from proximal end (101) of staple cartridge (37) and retainer cap (180) may be moved away from staple cartridge (37). With retainer cap (180) removed and with staple cartridge (37) properly seated in lower jaw (16) of end effector (12), instrument (10) may then be used in a surgical procedure.

III. Exemplary Fillable Buttress

A buttress (200), as shown in FIGS. 10-13, may be used with the end effector portion of the exemplary surgical cutter shown in FIGS. 1-6. It will be appreciated that use of buttress (200) as will be described below may facilitate quicker recovery to the surgical site where tissue has been severed and stapled by, for example, stabilizing areas where staples (47) have been applied. In some exemplary versions, buttress (200) may be used with retainer cap (180) described above, or alternatively, buttress (200) may be used directly with surgical severing and stapling instrument (10) described above without the use of retainer cap (180).

Figure 10:
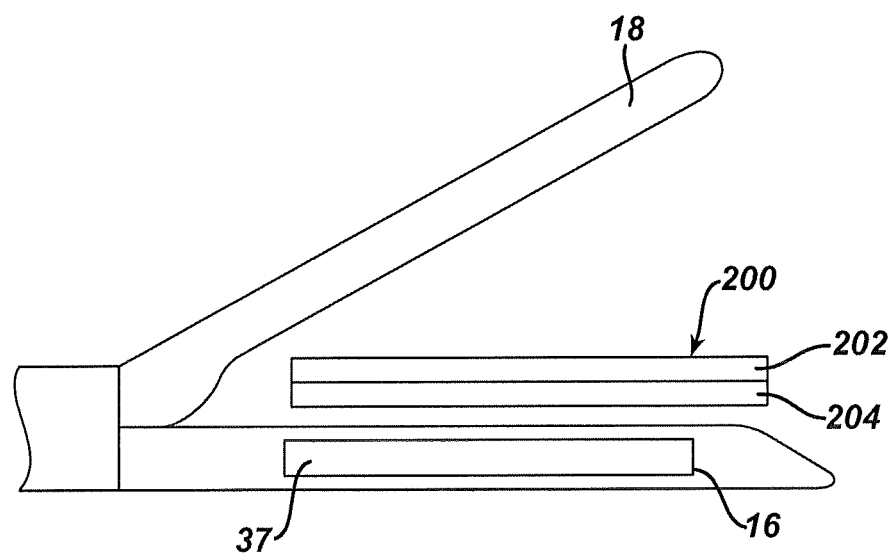
FIG. 10 depicts a side view of an exemplary end effector with a buttress.

FIG. 10 shows that buttress (200) comprises a first fluid fillable member (202) or bladder and a second fluid fillable member (204) or bladder. In some exemplary versions, first fluid fillable member (202) may be attached to anvil (18) by an adhesive and second fluid fillable member (204) may be attached to upper deck (72) of staple cartridge (37) positioned in lower jaw (16). In other exemplary versions, first fluid fillable member (202) and second fluid fillable member (204) may be adhered together and adhered to anvil (18). In other exemplary versions, first fluid fillable member (202) and second fluid fillable member (204) may be adhered together and adhered to upper deck (72) of staple cartridge (37). In some exemplary versions, rather than using an adhesive to attach first fluid fillable member (202) or second fluid fillable member (204) to anvil (18) and/or lower jaw (16), a clip or other suitable mechanical or liquid fastening system may be used as would be apparent to one of ordinary skill in the art in view of the teachings herein. The present example of FIG. 10 shows buttress (200) as it is about to be positioned between anvil (18) and lower jaw (16).

First fluid fillable member (202) and second fluid fillable member (204) contains a two-part liquid (220) such that when the two parts of liquid (220) come in contact with one another, as will be described below, they form a coagulant that buttresses the surgical site affected by surgical stapling and severing instrument (10) shown in FIGS. 1-6. In some exemplary versions, first fluid fillable member (202) is filled with fibrin while second fluid fillable member (204) is filled with thrombin, but it should be understood that any suitable material may be used. In some versions, first fluid fillable member (202) and second fluid fillable member (204) may both comprise liquid (220) that may be operable to buttress a surgical site without necessarily combining with another compound. In yet other exemplary versions, rather than two fluid fillable members, any suitable number of fluid fillable members may be used as would be apparent to one of ordinary skill in the art in view of the teachings herein. For example, three or more fluid fillable members may be used, or a single fluid fillable member may be used. Furthermore, buttress (200) may be prefilled with liquid (220) or alternatively the user or physician may fill buttress (200) with liquid (220) prior to use of surgical stapling and severing instrument (10). In some other exemplary versions, liquid (220) may comprise a hemostatic agent, a biologically safe glue, or any other suitable adhesive material as would be apparent to one of ordinary skill in the art in view of the teachings herein.

In the exemplary version, buttress (200) has a generally flat, rectangular shape configured to fit in between anvil (18) and lower jaw (16). Buttress (200) has a size at least slightly larger than the width of anvil (18) or lower jaw (16). In some exemplary versions, buttress (200) may have a size significantly larger than anvil (18) or lower jaw (16). However, any suitable shape or size for buttress (200) may be used as would be apparent to one of ordinary skill in the art in view of the teachings herein. Furthermore, buttress (200) comprises a semi self-supportive structure such that buttress (200) can maintain its generally flat shape when buttress (200) is not being compressed as will be discussed below.

Figure 11A:
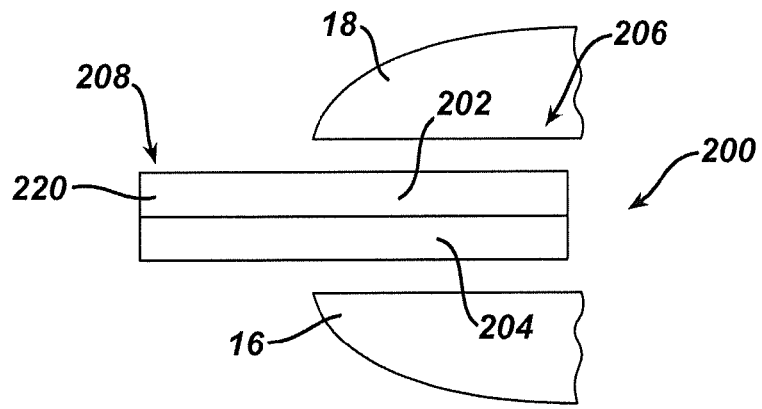
FIG. 11A depicts a front view of the buttress of FIG. 10 in an uncompressed state.
Figure 11B:
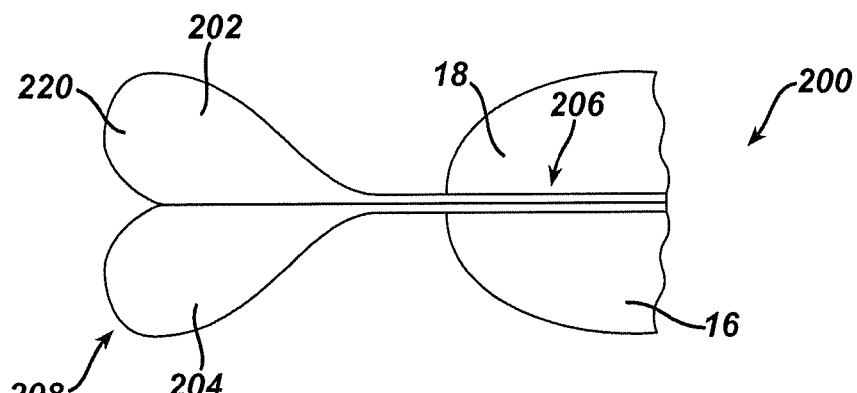
FIG. 11B depicts a front view of the buttress of FIG. 10 with an anvil and lower jaw clamped around buttress.
Figure 11C:
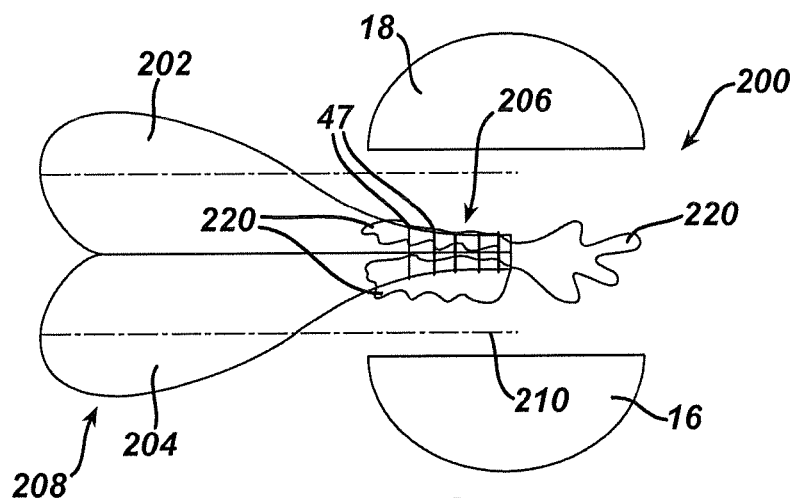
FIG. 11C depicts a side view of the buttress of FIG. 10 after being severed with liquid being urged from the buttress.

FIGS. 11A-C show a side view of buttress (200) showing how liquid (220) contained within first fluid filled portion (202) and second fluid filled portion (204) may be urged out of buttress (200). In the exemplary version, buttress (200) may be placed between anvil (18) and lower jaw (16) wherein buttress (200) remains mostly flat as shown in FIG. 11A. As also seen in FIG. 11A, liquid (220) remains in a substantially unpressurized state. In some exemplary versions, buttress (200) may be preloaded to be placed between anvil (18) and lower jaw (16) such that buttress (200) adheres to staple cartridge (not shown) contained in lower jaw (16). In other exemplary versions, the user or physician can load buttress (200) between anvil (18) and lower jaw (16) prior to use in a surgical setting. For example, in some exemplary versions the user may remove retaining cap (180) described above in FIGS. 7-9 and replace retaining cap (180) with buttress (200) prior to clamping anvil (18) and lower jaw (16) around the tissue of the surgical site. In other merely exemplary versions, buttress (200) may be coupled to retaining cap (180), wherein retaining cap (180) is removed prior to use, leaving only buttress (200) between anvil (18) and lower jaw (16). Other configurations for buttress (200) and retaining cap (180) may be used as would be apparent to one of ordinary skill in the art in view of the teachings herein.

FIG. 11B shows buttress (200) as it would appear when clamped by anvil (18) and lower jaw (16) resulting in a compressed region (206) and a pressurized region (208). In pressurized region (208), liquid (220) is forced under pressure. As seen in FIG. 11B, anvil (18) and lower jaw (16) have been clamped tightly around buttress (200) prior to buttress (200) being severed or stapled.

As seen in FIG. 11C, phantom lines (210) show the outline of buttress (200) prior to anvil (18) and lower jaw (16) compressing buttress (200). Anvil (18) and lower jaw (16) may be clamped to sandwich buttress (200). Liquid (220) contained within buttress (200) remains pressurized in pressurized region (208). While FIGS. 11B-11C show pressurized region (208) on one side of compressed region (206), it will be appreciated that an opposite pressurized region (208) could be formed on an opposite side of compressed (206). Buttress (200) comprises a generally elastic material configured to expand such that pressurized region (208) may be filled with most or all of the fluid in buttress (208) without breaking or popping under pressure. Pressurized region (208) accordingly expands beyond the region defined by phantom lines (210) to accommodate the increase in pressure and liquid of pressurized region (208).

As cutting edge (48) discussed above in reference to FIGS. 1-6 severs tissue (90), cutting edge (48) also severs buttress (200) resulting in buttress (200) being severed as shown in FIG. 11C. Almost simultaneously, buttress (200) is also stapled, and buttress (200) is thus ruptured by staples (47), thereby allowing buttress (200) to begin releasing liquid (220). Upon severing of buttress (200), liquid (220) is urged out of pressurized region (208) of buttress (200) and into the tissue of the surgical area thereby aiding in buttressing tissue (90) once tissue (90) is severed and stapled. Furthermore, staples (47) are deployed which, as stated above, further rupture buttress (200), thereby allowing liquid (220) to be squeezed out through regions of buttress (200) ruptured by staples (47) as well. In some exemplary versions, buttress (200) may comprise a dissolvable material such that buttress (200) may be left in tissue (90) without harming the patient. In other exemplary versions, buttress (200) may be removed from the surgical site once liquid (220) is released from buttress (200).

Figure 12A:
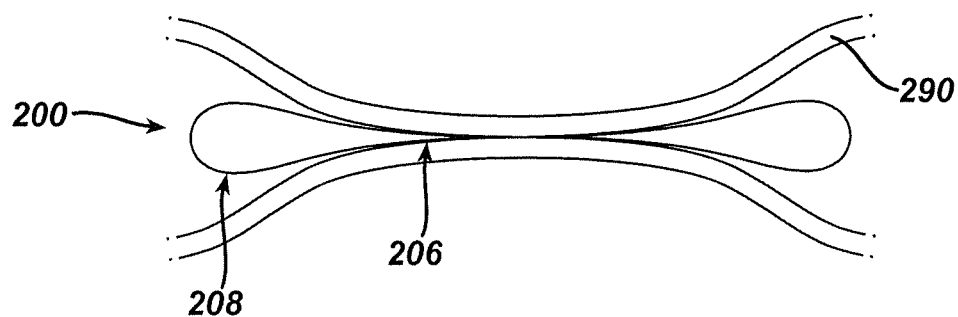
FIG. 12A depicts a front, cross-sectional view of the buttress of FIG. 10 being compressed.
Figure 12B:
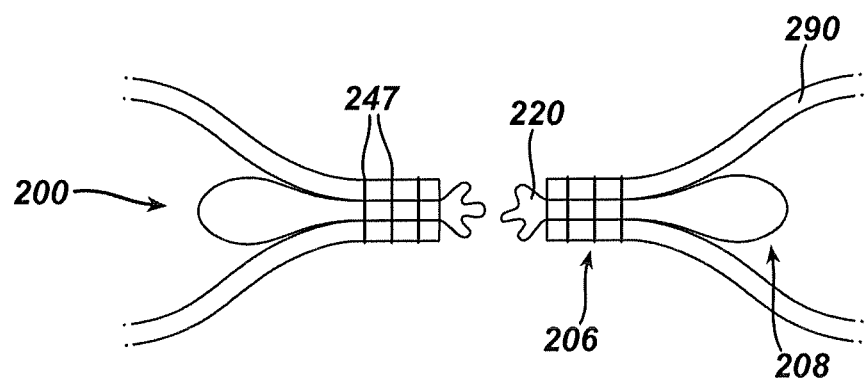
FIG. 12B depicts a front, cross-sectional view of the buttress of FIG. 10 after being severed.

FIGS. 12A-B show a front cross-sectional view of buttress (200) as it is being compressed between two layers of tissue (290). In some exemplary versions, buttress (200) may be sandwiched between tissue (290) or in some alternative versions, buttress (200) may be pressed against either the top surface or bottom surface of tissue (290). In some exemplary versions, the outer surface of buttress (200) may comprise an adhesive coating to allow buttress (200) to adhere to tissue (290) prior to release of liquid (220). FIG. 12B shows buttress (200) after being severed and stapled by staples (247) where pressurized region (208) containing liquid (220) urges liquid (220) through compressed region (206) into surrounding tissue (290). In some versions, liquid (220) may also be urged through ruptures caused by staples (247).

Figure 13:
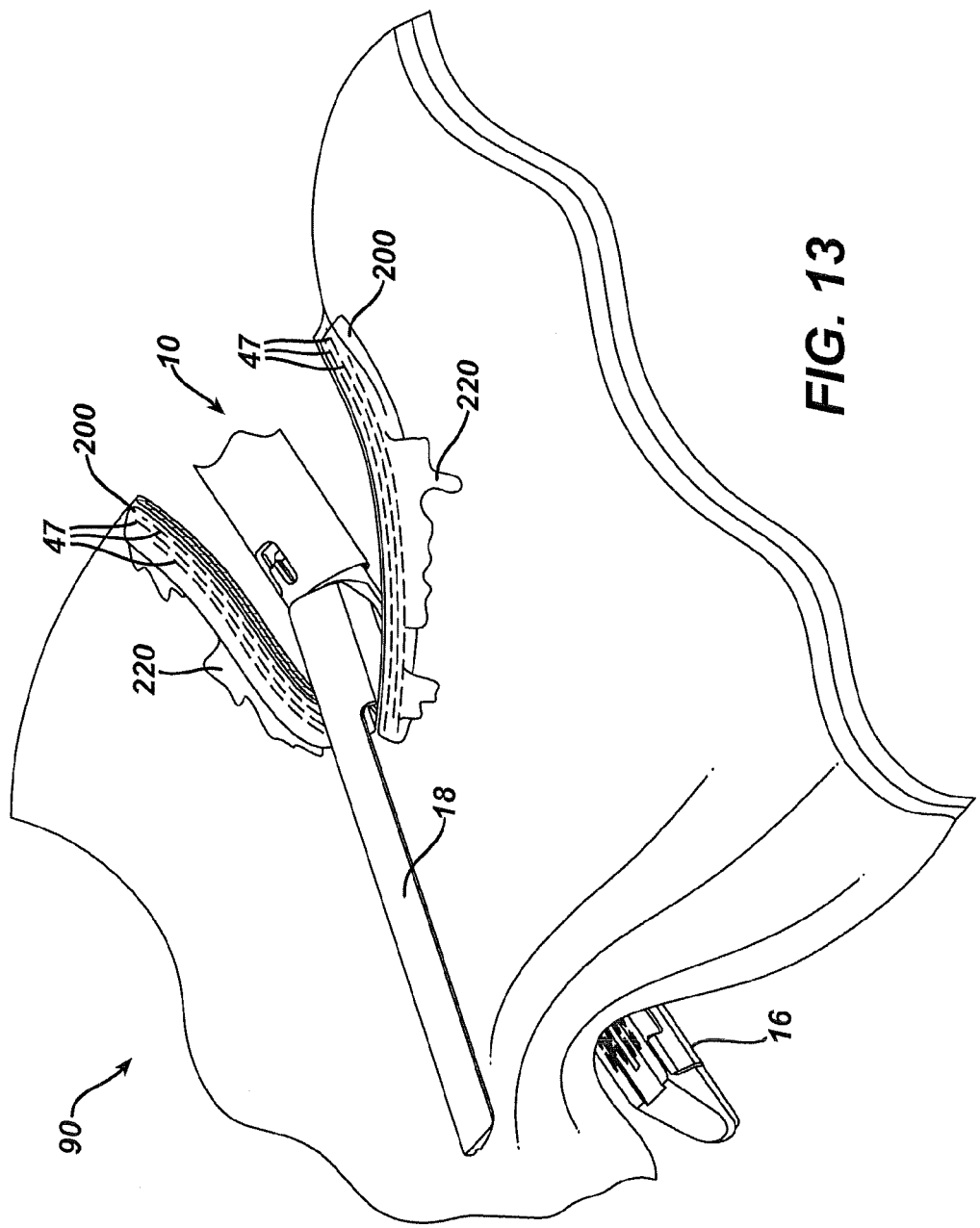
FIG. 13 depicts a perspective view of a surgical instrument with the buttress of FIG. 10 with liquid having been urged from the buttress.

FIG. 13 shows surgical severing and stapling instrument (10) as it is being used to sever and staple tissue (90). As can be seen in the present example, buttress (200) has been severed between anvil (18) and lower jaw (16). Furthermore, liquid (220) has been urged from buttress (200) into the surrounding tissue (90). While liquid (220) may comprise any suitable liquid, in the present example, liquid (220) comprises a coagulant, such as, for example, fibrin and thrombin. Liquid (220), once urged from buttress (200) is operable to aid in coagulation of the portions of tissue (90) where staples (47) have been inserted into tissue (90).

IV. Exemplary Buttress with Fillable Region

Figure 14:
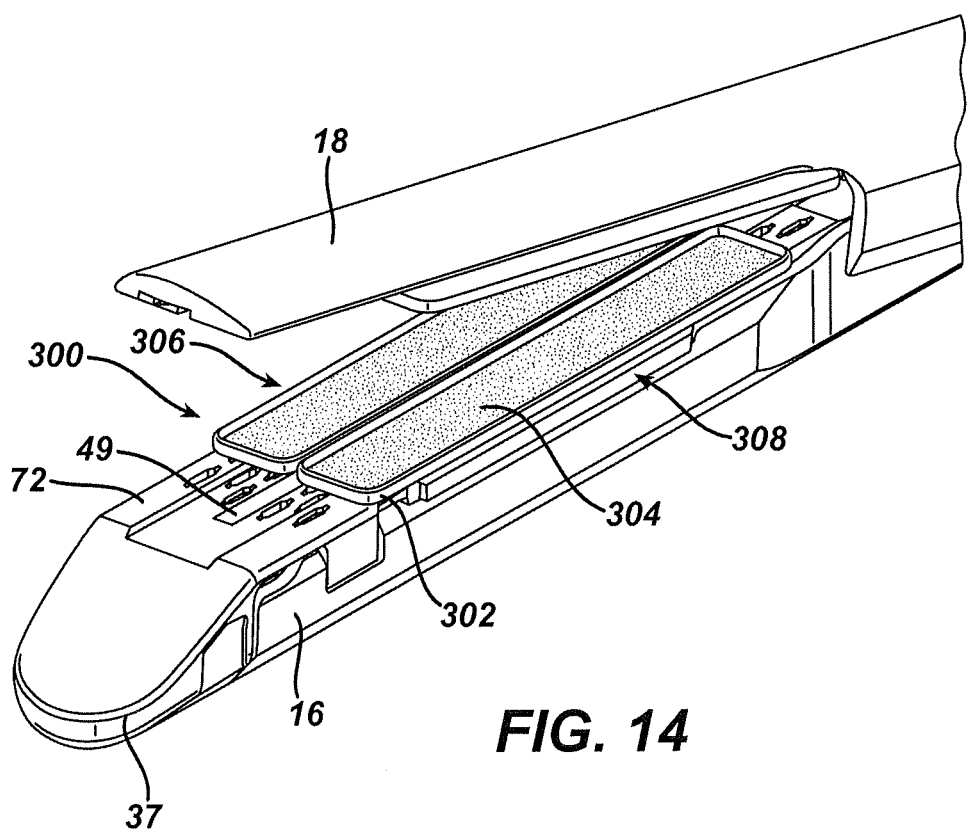
FIG. 14 depicts a perspective view of an exemplary end effector with an exemplary alternative version of a buttress.
Figure 15:
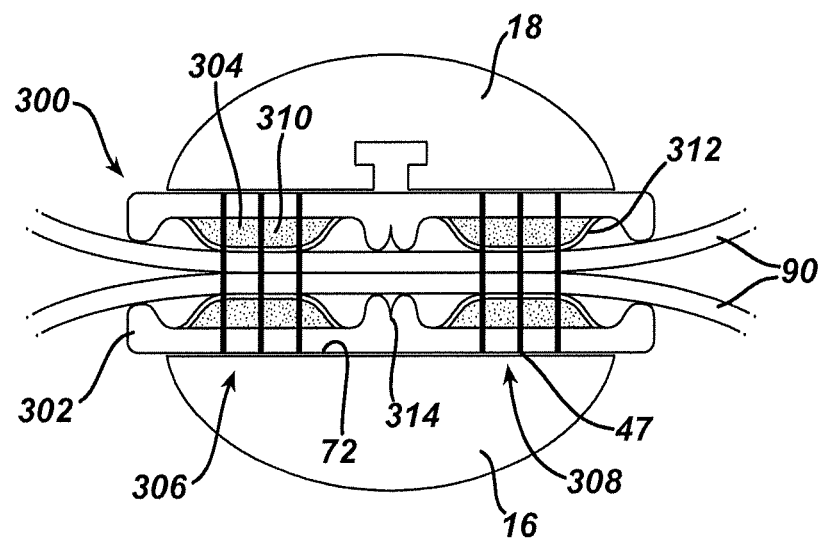
FIG. 15 depicts a cross sectional view of the exemplary end effector of FIG. 14 clamping tissue with a pair of buttresses.
Figure 16:
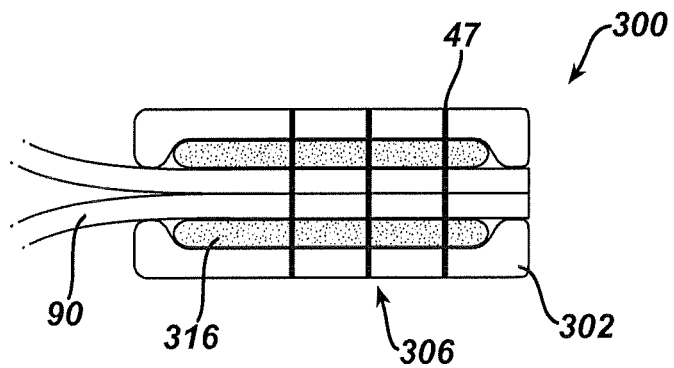
FIG. 16 depicts a cross sectional view of the pair of buttresses of FIG. 14 after being sliced by a cutting edge.

FIGS. 14-16 show a buttress (300) that may be used with end effector (12) of the instrument (10) shown in FIGS. 1-6. Buttress (300) comprises a barrier portion (302) and an adhesive region (304). Barrier portion (302) extends around the outer perimeter of adhesive region (304) thereby defining a first half (306) and a second half (308) of buttress (300). First half (306) and second half (308) are positioned such that vertical slot (49) is positioned roughly between first half (306) and second half (308). A cut line (314) extends between first half (306) and second half (308) as seen in FIG. 15 such that cutting edge (48) may cut barrier portion (302) along cut line (314). Of course, cut line (314) may be omitted. For instance, buttress (300) may be provided in discrete pieces on each side of vertical slot (49). Furthermore, it will be appreciated that buttress (300) may be configured as a single unit without the use of separate halves (306, 308). Similarly, while a single buttress (300) is used in the present example, it should be understood that two or more buttresses (300) may be used as would be apparent to one of ordinary skill in the art in view of the teachings herein. For example, FIG. 15 shows a cross sectional view of tissue (90) being clamped between two buttresses (300)—one buttress (300) on deck (72) of cartridge (37) and one buttress (300) on the underside of anvil (18).

Buttress (300) of the present example is constructed of a foam material, though it should be understood that any suitable materials may be used. By way of example only, buttress (300) may comprise a bio-absorbable fabric. Adhesive region (304) comprises an adhesive (310) held within an adhesive layer membrane (312). Adhesive (310) may comprise any suitable adhesive material as would be apparent to one of ordinary skill in the art in view of the teachings herein. For example, adhesive (310) may comprise cyanoarylates, anti-microbial agents, and/or healing agents. In yet other exemplary versions, adhesive regions (304) of halves (306, 308) may comprise two or more agents such that adhesive properties are only activated when the agents are combined after halves (306, 308) are punctured. Other suitable materials for adhesive (310) will be apparent to one of ordinary skill in the art in view of the teachings herein. Membrane (312) connected to barrier portion (302) forms a bubble configured to hold a fluid adhesive (310). For example, FIG. 15 shows membrane (312) enclosing adhesive (310). Membrane (312) may be constructed of a bio-absorbable plastic and/or other bio-absorbable material. Membrane (312) may further be constructed of any suitable material as would be apparent to one of ordinary skill in the art in view of the teachings herein.

As noted above, barrier portion (302) forms a lip around adhesive region (304) such that any fluids in adhesive region (304) are held within the perimeter defined by barrier portion (302). For example, as shown in FIGS. 15-16, tissue (90) that is clamped between two buttresses (300) is positioned such that adhesive regions (304) face toward tissue (90). Anvil (18) is clamped against lower jaw (16) such that buttresses (300) squeeze tissue (90), thereby forming a seal between barrier portion (302) and tissue (90). As seen in FIG. 15, staples (47) pierce through membrane (312) of adhesive region (304). As a result, adhesive region (304) ruptures and adhesive (310) flows out. Barrier portion (302) has a cup-like shape configured to hold adhesive (310) against tissue (90) after adhesive (310) leaves adhesive region (304); while substantially preventing adhesive (310) from flowing out of buttress (300) to surrounding tissue. FIG. 16 shows adhesive (310) after it has flown out from adhesive region (304) and formed an adhesive layer (316). Also in FIG. 16, cutting edge (48) has sliced along cut line (314) severing tissue (90). It will be appreciated that staples (47) operably hold buttresses (300) pressed against tissue (90).

Figure 17:
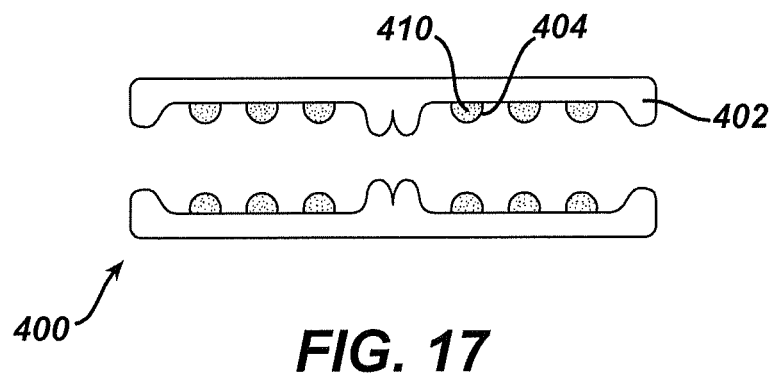
FIG. 17 depicts a cross sectional view of an exemplary alternative buttress having a plurality of adhesive regions.

FIG. 17 shows an exemplary alternative version of buttress (400) having a plurality of adhesive regions (404) spaced apart within barrier portion (402). Adhesive regions (404) comprise plastic modules operable to burst when punctured and/or when sufficiently compressed. Each adhesive regions (404) has an adhesive (410) contained therein. It will be appreciated that all of the adhesive regions (404) need not necessarily contain the same adhesives (410). For example, some adhesive regions (404) may comprise one type of adhesive (410) and/or therapeutic material whereas other adhesive regions (404) may comprise a different type of adhesive (410) and/or therapeutic material. Of course, any other suitable medical fluids may be included in regions (404) in addition to or in lieu of adhesives.

Figure 18:
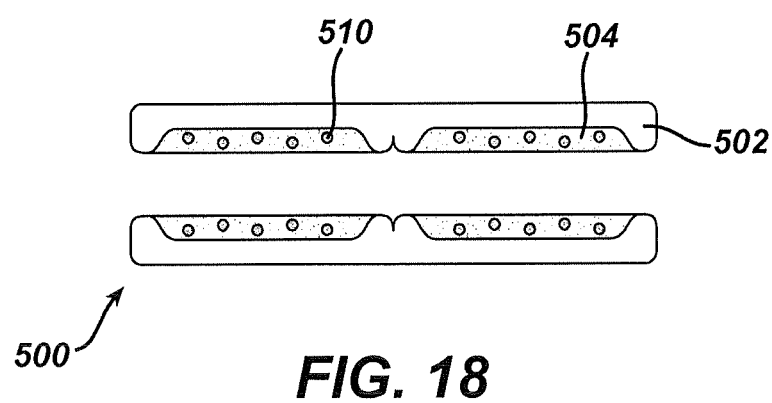
FIG. 18 depicts a cross sectional view of an exemplary alternative buttress having a plurality of adhesive capsules.

FIG. 18 shows yet another exemplary version of buttress (500) having a foam region (504), with adhesive capsules (510) embedded and/or seeded into foam region (504). Foam region (504) is contained within barrier portion (502). Foam region (504) may substantially prevent adhesive capsules (510) from inadvertently leaving buttress (500) before buttress (500) is deployed at a surgical site. Foam region (504) may also substantially prevent adhesive that is released from capsules (510) from escaping the surgical site after buttress (500) is deployed at the surgical site. Furthermore, foam region (504) may substantially prevent the adhesive (510) of capsules (510) from sticking to anvil (18) and/or cartridge (18), before and/or after buttress (500) is deployed at the surgical site.

Figure 19:
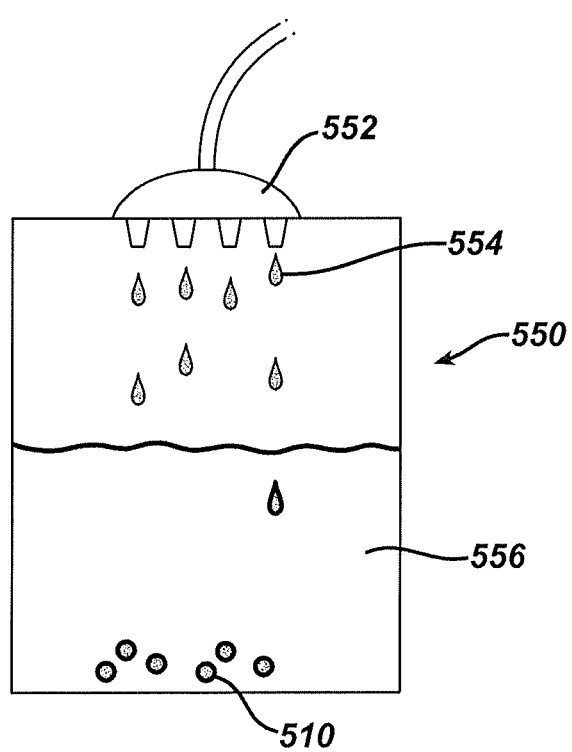
FIG. 19 depicts a cross sectional view of an exemplary capsule forming chamber for forming the plurality of adhesive capsules of FIG. 18.

Adhesive capsules (510) may be constructed from any suitable method as would be apparent to one of ordinary skill in the art in view of the teachings herein. FIG. 19 shows one exemplary way of making adhesive capsules (510) using a capsule forming chamber (550). Chamber (550) comprises a dispenser (552) and coating medium (556). It will be appreciated that any non-reactive gas may be contained within chamber (550). Dispenser (552) dispenses adhesive material (554), which falls as adhesive drops before entering coating medium (556). Coating medium (556) may comprise a plastic, but any suitable material may be used as would be apparent to one of ordinary skill in the art in view of the teachings herein. Adhesive material (554) contacts coating medium (556) and becomes covered with a coating, thereby forming adhesive capsules (510) at the bottom of coating medium (556). Thereafter, adhesive capsules (510) may be removed from chamber (550) and placed into foam region (504) as shown in FIG. 18. Of course, adhesive capsules (510) may be formed from any other suitable method as would be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
    (a) a surgical cutter comprising a distal end and a proximal end, wherein the proximal end comprises a handle, wherein the distal end comprises an anvil and a lower jaw, wherein the anvil and the lower jaw are configured to clamp tissue, wherein the surgical cutter is configured to sever tissue clamped by the anvil and the lower jaw; and
    (b) a buttress filled with a liquid, wherein the buttress is configured to be placed between the anvil and the lower jaw, wherein the buttress is configured to transition between a first configuration and a second configuration, wherein a height of the buttress is generally constant along a width of the buttress in the first configuration, wherein the anvil and the lower jaw are operable to clamp the buttress to reach the second configuration, wherein the buttress includes a compressive portion and a pressure portion in the second configuration, the pressure portion having a greater height than the compressive portion, wherein the compressive portion extends outwardly from the anvil and lower jaw, wherein the buttress is configured to be severed and stapled by the surgical cutter substantially contemporaneously with when the surgical cutter severs tissue, wherein the pressure portion is configured to urge the liquid through the compressive portion only once the buttress is severed.

2. The apparatus of claim 1, wherein the liquid comprises a two-part adhesive configured to have adhesive properties only once the two parts of the two-part adhesive are combined.

3. The apparatus of claim 1, wherein the buttress comprises an elastic material.

4. The apparatus of claim 1, wherein the anvil defines an anvil width, wherein the buttress defines a buttress width that is wider than the anvil width.

5. The apparatus of claim 1, wherein the buttress comprises a resilient material.

6. The apparatus of claim 1, wherein the buttress has a generally rectangular shape.

7. The apparatus of claim 1, wherein the buttress is configured to be pre-loaded into the surgical cutter.

8. The apparatus of claim 1, wherein the buttress straddles the lower jaw such that a substantially equal portion of the buttress extends outward from the lower jaw.

9. The apparatus of claim 1, wherein the buttress is configured to be coupled to the lower jaw.

10. The apparatus of claim 1, wherein the buttress comprises two substantially similarly shaped fluid filled members, wherein each of the two fluid filled members comprise a liquid adhesive.

11. The apparatus of claim 10, wherein each of the two fluid filled members comprises different liquid components.

12. The apparatus of claim 1, further comprising a surgical stapler in communication with the surgical cutter, wherein the surgical stapler comprises one or more staples, wherein the surgical stapler is configured to staple a portion of tissue, wherein the one or more staples are configured to rupture the buttress.

13. The apparatus of claim 1, wherein the buttress comprises a dissolvable material.

14. The apparatus of claim 1, wherein the buttress comprises a two-part fluid coagulant, wherein one of the two-part fluids comprises fibrin, wherein the other of the two-part fluids comprises thrombin.

15. The apparatus of claim 1, wherein the buttress comprises an adhesive on the outside of the buttress operable to adhere the buttress to a portion of the surgical cutter.

16. An apparatus comprising:
(a) a surgical instrument comprising a cutter and a stapler, wherein the surgical instrument further comprises an anvil and a lower jaw operable to compress tissue as the tissue is cut and stapled, wherein the cutter is configured to cut at least a portion of the tissue, wherein the stapler is configured to staple at least a portion of the tissue; and
(b) a pair of bladders, wherein at least a portion of the pair of bladders is positioned between the anvil and the lower jaw, wherein the pair of bladders comprises a first bladder and a second bladder adhered to one another, wherein the first bladder contains a first coagulant component, wherein the second bladder contains a second coagulant component, wherein the cutter is operable to simultaneously rupture both the first bladder and the second bladder, thereby mixing at least a portion of the first coagulant component with at least a portion of the second coagulant component.

17. The apparatus of claim 16, wherein at least one of the pair of bladders further contains a fluid adhesive.

18. The apparatus of claim 16, wherein the anvil and the lower jaw is configured to compress at least a portion of the pair of bladders.

19. The apparatus of claim 16, wherein each of the pair of bladders comprises an elastic material.

20. An apparatus comprising:
(a) a surgical instrument comprising a cutting feature and a stapling feature, wherein the cutting feature is configured to cut at least a portion of the tissue, wherein the stapling feature is configured to staple at least a portion of the tissue, wherein the stapling feature comprises an anvil and a lower jaw operable to compress tissue as the tissue is cut and stapled, wherein the stapling feature further comprises staples; and
(b) a buttress comprising a barrier region and an adhesive region, the adhesive region including adhesive and a membrane covering at least a portion of the adhesive, wherein the barrier region forms a lip extending around the perimeter of the adhesive region to thereby contain the adhesive;
wherein cutting feature is configured to sever a portion of the barrier region, wherein the staples are configured to pierce the membrane and allow adhesive to flow, wherein the lip is configured to prevent flowing adhesive from leaving the buttress when the buttress is pressed against tissue.

* * * * *